United States Patent [19]

Engelhorn et al.

[11] Patent Number: 5,578,180
[45] Date of Patent: Nov. 26, 1996

[54] SYSTEM FOR PH-NEUTRAL LONGLIFE PRECAST ELECTROPHORESIS GEL

[75] Inventors: Sheldon Engelhorn, Encinitas; Timothy V. Updyke, Temecula, both of Calif.

[73] Assignee: Novel Experimental Technology, San Diego, Calif.

[21] Appl. No.: 221,939

[22] Filed: Mar. 31, 1994

[51] Int. Cl.$^6$ .................................................... G01N 27/26
[52] U.S. Cl. ........................... 204/468; 204/469; 204/470
[58] Field of Search ............................ 204/182.8, 299 R, 204/468, 469, 456, 470; 530/427; 422/82.01

[56] References Cited

U.S. PATENT DOCUMENTS

| | | | |
|---|---|---|---|
| 3,870,812 | 3/1975 | Hayes, Jr. et al. | 426/350 |
| 3,948,743 | 4/1976 | Monthony | 204/180 G |
| 4,139,440 | 2/1979 | Chrambach | 204/180 G |
| 5,370,777 | 12/1994 | Guttman et al. | 204/182.8 |

OTHER PUBLICATIONS

K. Nakamura et al., Electrophoresis 1989, 10, 29–33.
Abstract, R. Ruechel et al., Hoppe–Seyler's Z. Physiol. Chem., 356(8), 1283–8, 1975.
A. T. Andrews, Electrophoresis, Oxford Univ. Press, 1986 pp. 20 & 126.
Andrews, Anthony T., "Electrophoresis, Theory, Techniques, and Biochemical and Clinical Applications", *Oxford Science Publications*, Second Edition, (1986), pp. 79–92.
Chrambach, Andreas and Jovin, Thomas M., "Selected buffer systems for moving boundary electrophoresis on gels at various pH values, presented in a simplified manner", *Electrophoresis*, (1983), vol. 4, pp. 190–204.
Christy, Kenneth G., Jr., LaTart, David B., and Osterhoudt, Hans W., "Modifications for SDS–Page of Proteins", *BioTechniques*, vol. 7, No. 7, (1989), pp. 692–693.
Fritz, Jeffery, D., Swartz, Darl R., and Greaser, Marion L., "Factors Affecting Polyacrylamide Gel Electrophoresis and Electroblotting of High–Molecular–Weight Myofibrillar Proteins", *Analytical Biochemistry*, vol. 180, (1989), pp. 205–210.
Hames, B. D. and Rickwood, D., "Gel Electrophoresis of Proteins, A Practical Approach" *The IRL Press at Oxford University Press*, Second Edition, (1990), pp. 1–50.
Hunkapiller, Michael W., Lujan, Eva, Ostrander, Frank, and Hood, Leroy E., "Isolation of Microgram Quantities of Proteins from Polyacrylamide Gels for Amino Acid Sequence Analysis", *Methods in Enzymology*, vol. 91, (1983), pp. 227–232.

Jovin, Thomas M., "Multiphasic Zone Electrophoresis. I, II & III Steady–State Moving–Boundary Systems Formed by Different Electrolyte Combinations", *Biochemistry*, vol. 12, No. 5, (1973), pp. 871–898.
Jovin, Thomas M., "Multiphasic Zone Electrophoresis. IV. Design and Analysis of Discontinuous Buffer Systems with a Digital Computer", *Annals New York Academy of Science, Jovin: Computer Design of Buffer Systems*, (1973), pp. 477–496.
Kyte, Jack and Rodriguez, Henry, "A Discontinuous Electrophoretic System for Separating Peptides on Polyacrylamide Gels", *Academic Press, Inc.*, (1983), pp. 515–522.
Lane, Leslie C., "A Simple Method for Stabilizing Protein–Sulfhydryl Groups during SDS–Gel Electrophoresis", *Analytical Biochemistry*, vol. 86, (1978), pp. 655–664.
Martin de Llano, J. Javier and Gavilanes, Jose G., "Increased electrophoretic mobility of sodium sulfite–treated jack bean urease", *Electrophoresis*, vol. 13, (1992), pp. 300–304.
Moos, Malcolm, Jr., Nguyen, Nga Yen, and Liu, Teh–Yung, "Reproducible High Yield Sequencing of Proteins Electrophoretically Separated and Transferred to an Inert Support", *The Journal of Biological Chemistry*, vol. 263, No. 13, (1988), pp. 6005–6008.
Wiltfang, Jens, Arold, Norbert, and Nuehogg, Volker, "A new multiphasic buffer system for sodium dodecly sulfate–polyacrylamide gel electrophoresis of proteins and peptides with molecular masses 100 000–1000, and their detection with picomolar sensitivity", *Electrophoresis*, vol. 12, (1991), pp. 352–366.
"Electrophoresis, The NOVEX System: the Fast, Easy Way To Your Answer!", NOVEX Brochure (1992).
"Technically Speaking . . . , NOVEX Pre–mixed Buffers, Fast, Easy, Reproducible Electrophoresis Buffers", NOVEX Brochure (1993).
"Migration Tables" and Buffer Selection Guide, NOVEX Brochure, (1991).

*Primary Examiner*—T. Tung
*Assistant Examiner*—Alex Noguerola
*Attorney, Agent, or Firm*—Fish & Neave

[57] ABSTRACT

A gel and buffer system for gel electrophoresis wherein separation occurs at neutral pH and proteins remain completely reduced.

17 Claims, No Drawings

SYSTEM FOR PH-NEUTRAL LONGLIFE PRECAST ELECTROPHORESIS GEL

This invention relates to techniques for gel electrophoresis. More particularly this invention relates to a novel system for gel electrophoresis at approximately neutral pH.

BACKGROUND OF THE INVENTION

Gel electrophoresis is a common procedure for the separation of biological molecules, such as DNA, RNA, polypeptides and proteins. In gel electrophoresis, the molecules are separated into bands according to the rate at which an imposed electric field causes them to migrate through a filtering gel.

The basic apparatus used in this technique consists of a gel enclosed in a glass tube or sandwiched as a slab between glass or plastic plates. The gel has an open molecular network structure, defining pores which are saturated with an electrically conductive buffered solution of a salt. These pores through the gel are large enough to admit passage of the migrating macromolecules.

The gel is placed in a chamber in contact with buffer solutions which make electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel. The locations of the bands of separated macromolecules are then determined. By comparing the distance moved by particular bands in comparison to the tracking dye and macromolecules of known mobility, the mobility of other macromolecules can be determined. The size of the macromolecule can then be calculated.

The rate of migration of macromolecules through the gel depends upon three principle factors: the porosity of the gel; the size and shape of the macromolecule; and the charge density of the macromolecule. It is critical to an effective electrophoresis system that these three factors be precisely controlled and reproducible from gel to gel and from sample to sample. However, maintaining uniformity between gels is difficult because each of these factors is sensitive to many variables in the chemistry of the gel system.

Polyacrylamide gels are commonly used for electrophoresis. Polyacrylamide gel electrophoresis or PAGE is popular because the gels are optically transparent, electrically neutral and can be made with a range of pore sizes. The porosity of a polyacrylamide gel is in part defined by the total percentage of acrylamide monomer plus crosslinker monomer ("% T") it contains. The greater the concentration, the less space there is between strands of the polyacrylamide matrix and hence the smaller the pores through the gel. An 8% polyacrylamide gel has larger pores than a 12% polyacrylamide gel. An 8% polyacrylamide gel consequently permits faster migration of macromolecules with a given shape, size and charge density. When smaller macromolecules are to be separated, it is generally preferable to use a gel with a smaller pore size such as a 20% gel. Conversely for separation of larger macromolecules, a gel with a larger pore size is often used, such as an 8% gel.

Pore size is also dependent upon the amount of crosslinker used to polymerize the gel. At any given total monomer concentration, the minimum pore size for a polyacrylamide gel is obtained when the ratio of total monomer to crosslinker is about 20:1, (the usual expression for this ratio would be "5% C").

Several factors may cause undesirable variation in the pore size of gels. Pore size can be increased by incomplete gel polymerization during manufacture. Hydrolysis of the polyacrylamide after polymerization can create fixed negative charges and break down the crosslinks in the gel, which will degrade the separation and increase the pore size. An ideal gel system should have a reproducible pore size and no fixed charge (or at least a constant amount) and should be resistant to change in chemical characteristics or the pore size due to hydrolysis.

The size of the macromolecule varies between different macromolecules; the smaller and more compact the macromolecule the easier it will be for the macromolecule to move through the pores of a given gel. Given a constant charge density, the rate of migration of a macromolecule is inversely proportional to the logarithm of its size.

For accurate and reproducible electrophoresis, a given type of macromolecule should preferably take on a single form in the gel. One difficulty with maintaining uniformity of the shape of proteins during gel electrophoreses is that disulfide bonds can be formed by oxidation of pairs of cysteine amino acids. Different oxidized forms of the protein then have different shapes and, therefore, migrate through the gel run with slightly different mobilities (usually faster than a completely reduced protein, since the maximum stokes radius and minimum mobility should occur with a completely unfolded form). A heterogeneous mixture of forms leads to apparent band broadening. In order to prevent the formation of disulfide bonds, a reducing agent such as dithiothreitol (DTT) is usually added to the samples to be run.

The charge density of the migrating molecule is the third factor affecting its rate of migration through the gel—the higher the charge density, the more force will be imposed by the electric field upon the macromolecule and the faster the migration rate subject to the limits of size and shape. In SDS-PAGE electrophoresis the charge density of the macromolecules is controlled by adding sodium dodecyl sulfate ("SDS") to the system. SDS molecules associate with the macromolecules and impart a uniform charge density to them substantially negating the effects of any innate molecular charge.

SDS PAGE gels are usually poured and run at basic pH. The most common PAGE buffer system employed for the separation of proteins is that developed by Ornstein (1) and modified for use with SDS by Laemmli (2). Laemmli, U.K. (1970) *Nature* 227, 680–686. The Laemmli buffer system consists of 0.375M Tris (tris (hydroxy methyl) aminomethane), titrated to pH 8.8. with HCl, in the separating gel. The stacking gel consists of 0.125M Tris, titrated to pH 6.8. The anode and cathode running buffers contain 0.024M Tris, 0.192M glycine, 0.1% SDS. An alternative buffer system is disclosed by Schaegger and von Jagow. Schaegger, H. and von Jagow, G., *Anal. Biochem.* 1987, 166, 368–379. The stacking gel contains 0.75M Tris, titrated to pH 8.45 with HCl. The separating gel contains 0.9M Tris, titrated to pH 8.45 with HCl. The cathode buffer contains 0.1M Tris, 0.1M Tricine, 0.1% SDS. The anode buffer contains 0.2M Tris, titrated to pH 8.9 with HCl. For both of these systems Tris is the "common ion" which is present in the gel and in the anode and cathode buffers.

In the Laemmli system, the pH of the trailing phase in the stacking gel is about 8.9. In the separating gel, the trailing phase pH is about 9.7. At this pH, primary amino groups of proteins react readily with unpolymerized acrylamide, thiol groups are more subject to oxidation to disulfides, or reaction with unpolymerized polyacrylamide, than at neutral pH and acrylamide itself is subject to hydrolysis.

The need for uniformity and predictability is magnified in precast electrophoresis gels which are manufactured by an outside vendor and then shipped to the laboratory where the electrophoresis will be performed. Precast gels must control the properties discussed above and they must be able to maintain this control throughout shipping and storage. The shelf life of many precast gels is limited by the potential for hydrolysis of acrylamide during storage at the high pH of the gel buffer.

It is a disadvantage of a high pH gel that the polyacrylamide gel is subject to degradation by hydrolysis and has a limited shelf-life.

It is a further disadvantage of a high pH gel that proteins react readily with unpolymerized acrylamide which may interfere with subsequent analysis of the protein such as peptide sequencing.

It is a still further disadvantage of a high pH gel that thiol groups are subject to oxidation to disulfides causing a decreased resolution of separated macromolecules.

SUMMARY OF THE INVENTION

It is an object of this invention to produce a neutral gel system that reduces protein reaction with unpolymerized acrylamide thereby enhancing yield and resolution.

It is a further object of this invention to produce a neutral gel system that prevents formation of disulfides from free thiol groups thereby enhancing yield and resolution.

It is a still further object of this invention to produce a neutral gel system that reduces degradation of the polyacrylamide gel by hydrolysis thereby increasing the useful shelf-life of a precast gel.

In accordance with this invention, applicants describe a gel and buffer system wherein separation occurs at neutral pH and proteins remain completely reduced. The above and other objects and advantages of the present invention will be apparent upon consideration of the following detailed description.

DETAILED DESCRIPTION OF THE INVENTION

Applicants describe a gel and buffer system wherein separation occurs at neutral pH and proteins remain completely reduced. Advantageously, at this neutral pH, primary amino groups of proteins react less readily with unpolymerized acrylamide because protonation of protein amino groups greatly reduces their reactivity to acrylamide or other related blocking agents. Furthermore, at this neutral pH, thiol groups are less subject to oxidation than at higher pH and polyacrylamide itself is less subject to hydrolysis.

The result is a gel system with improved stability of the gel matrix and stock solutions. Gels prepared according to this system can be stored under refrigeration for over a year without loss of performance due to acrylamide hydrolysis. Also, stock buffers without reducing agents and stock gel solutions without polymerization initiator can be stored for at least several weeks at room temperature with no loss of performance. An additional benefit is that a single gel recipe, using the same buffer for the stacking and separating gels, can be used with two different running buffers to give two separation systems. Using this feature, an 8% gel, for example, can cover a protein separation range of 2 to 200 kDa.

In one embodiment of this invention a polyacrylamide gel of between about 3% and about 25% (% T) acrylamide is polymerized using from about 1% to about 6% crosslinker (% C) using a gel buffer comprising a primary organic amine or substituted amine with a pK near neutrality, titrated with approximately half as much HCl (on a molar basis), so that the pH of the buffer is approximately neutral. In a preferred embodiment the gel is polymerized using from about 2% to about 5% crosslinker (% C) using a gel buffer comprising Bis-Tris[Bis-(2-hydroxyethyl)iminotris(hydroxymethyl)methane] titrated with HCl. Different separation characteristics can be obtained by running the gel with either a MOPS (3-[N-Morpholino]propanesulfonic acid) or MES (2-(N-Morpholino)ethanesulfonic acid), buffer. 2 mM to 10 mM TGA or 2 mM to 10 mM sodium bisulfite is added to the running buffer to maintain a reducing environment in the gel during electrophoresis. This and other embodiments can be understood by reference to the following illustrative and comparative examples.

EXAMPLES

Bis-Tris, MES, and MOPS were purchased from Sigma (St. Louis, Mo.) or Research Organics (Cleveland, Ohio). Thioglycolic acid (TGA), DTT and mercaptoethanol (BME) were from Sigma. All other chemicals were reagent, "ultra pure" or "electrophoresis grade" from standard sources. Gels were cast in 1 mm thickness mini-gel cassettes from Novex (San Diego Calif.) and run in a Novex minicell.

The Bis-Tris separating gel and stacking gels were prepared from a 30% T/2.5% C acrylamide/BIS stock solution and a 7× Bis-Tris stock solution (2.5M Bis-Tris, 1.5M HCl, pH 6.5). To prepare the separating gel, the stock solutions were blended with ultra pure water to a final concentration 8% T, 0,357M Bis-Tris, to which was added 0.2 ul/ml temed. After degassing, 2.0 ul/ml of a10% solution of APS was added, the gel was immediately poured into the cassette then overlaid with water. Polymerization was allowed to proceed for at least 30 minutes at RT, the water was removed and a 4% stacking gel applied. The stacking gel was prepared in the same fashion as the separating gel, except that the final concentration obtained was 4% T, temed concentration was increased to 0.4 ul/ml and the APS increased to 5.0 ul/ml.

MOPS running buffer consisted of 50 mM MOPS, 50 mM Bis-Tris (or TRIS), 0.1% SDS, 1 mM EDTA. MES running buffer consisted of 50 mM MES, 50 mM Bis-Tris (or TRIS), 0.1% SDS, 1 mM EDTA. Sample buffer (2×) consisted of 0.25M Bis-Tris, 0.15M HCl, 10% (w/v) Glycerol, 2% SDS, 1 mM EDTA, 0.03% Serva Blue G, and 200 mM DTT. Samples containing a set of protein standards were heated for 15 min at 70 degrees before application. Bovine serum albumin (BSA), chicken egg ovalbumin, alkylated insulin A and B chain, soybean trypsin inhibitor, and bovine erythrocyte carbonic anhydrase were included in the standard. Sample volume was 5 ul in all cases.

Example 1

The protein standards were separated on an 8% Bis-Tris gel with MOPS running buffer in the absence of a reducing agent. The resulting separation pattern was very similar to that obtained on an 8% TRIS/glycine gel (Laemmli), with proteins 20,000 and smaller remaining in the stack along with the tracking dye. The BSA band was somewhat diffuse and shifted toward the anode. The Ovalbumin band was also somewhat diffuse.

Example 2

The protein standards were separated on an 8% Bis-Tris gel with MOPS running buffer in the presence of TGA in the cathode buffer. Again, the separation pattern was very similar to that obtained on an 8% TRIS/glycine (Laemmli) gel, with proteins 20,000 and smaller remaining in the stack along with the tracking dye. The presence of the reducing agent, 5 mM TGA, in the cathode buffer provided for better resolution of the proteins BSA and Ovalbumin compared to the gel run without TGA.

Example 3

The protein standards were separated on an 8% Bis-Tris gel with MOPS running buffer in the presence of sodium bisulfite in the cathode buffer. Again, the separation pattern was very similar to that obtained on an 8% TRIS/glycine (Laemmli) gel, with proteins 20,000 and smaller remaining in the stack along with the tracking dye. The presence of the reducing agent, 5 mM sodium bisulfite, in the cathode buffer provided for better resolution of the proteins BSA and Ovalbumin compared to the gel run without sodium bisulfite.

Example 4

The protein standards were separated on an 8% Bis-Tris gel with MES running buffer in the absence of a reducing agent. The protein separation was very similar to that obtained from a 12% TRIS/tricine (Schaegger) gel. All proteins were resolved from the stack including insulin A and B chain (3500 and 2500 daltons, respectively). When the gel is run without TGA, soybean trypsin inhibitor had a more prominent doublet.

Example 5

The protein standards were separated on an 8% Bis-Tris/Cl gel with Bis-Tris/MES running buffer in the presence of TGA in the cathode buffer. Again, all proteins were resolved from the stack including insulin A and B chain (3500 and 2500 daltons, respectively). The presence of the reducing agent, 5 mM TGA, in the cathode buffer provided for better resolution of the protein soybean trypsin inhibitor. Carbonic anhydrase ran as a tight, sharp band under all conditions tested.

Example 6

The protein standards were separated on an 8% Bis-Tris/Cl gel with Bis-Tris/MES running buffer in the presence of sodium bisulfite in the cathode buffer. Again, all proteins were resolved from the stack including insulin A and B chain (3500 and 2500 daltons, respectively). The presence of the reducing agent, 5 mM sodium bisulfite, in the cathode buffer provided for better resolution of the protein soybean trypsin inhibitor. Carbonic anhydrase ran as a tight, sharp band under all conditions tested.

Although MES and MOPS were selected as desirable running buffers because the resulting system has separation characteristics similar to the commonly used Laemmli and Schaegger gel systems, it was found that a range of buffers are suitable for use in this system. Among the additional buffers giving good results were ACES ([N-(2-Acetomido)]-2-aminoethanesulfonic acid, MOPSO (2-[N-Morpholino]-2-hydroxypropanesulfonic acid, TES (N-Tris-(hydroxymethyl)-2-ethanesulfonic acid, BES (N,N-BIS-(Hydroxyethyl)-2-aminoethanesulfonic acid, HEPES (N-2-Hydroxyethyl-piperazine-n-2-ethanesulfonic acid), TAPSO (3-(N-tris-(Hydroxymethyl)methylamino)-2-hydroxypropanesulfonic acid.

All the proteins that exhibit some band broadening and/or mobility shifts when run in the absence of TGA or sodium bisulfite, have in common a composition that includes multiple cysteines (BSA, for instance, has 35 cysteines). On the other hand carbonic anhydrase, which always runs cleanly, has no cysteines. Moreover, if the reduced proteins are alkylated before running, they run as sharp homogeneous bands even in the absence of a reducing agent.

Cysteine-containing proteins appear to give generally sharper bands in the Laemmli system than the neutral system, when both are run with 100 mM mercaptoethanol or DTT in the sample buffer but without TGA in the running buffer. Since thiol oxidation is more favored as the pH increases, it would be expected that the higher pH of the Laemmli system would cause oxidation of disulfide to be at least as pronounced as it is in the neutral pH system. However, DTT and similar "neutral" thiol reducing agents are weak acids (with pKa's around pH 8–9). Thus, at basic pH, these reducing agents migrate into the gel and, if present at sufficient concentration, provide some protection against oxidation of sulfhydryls. At a neutral separating pH, DTT from the sample buffer is in an uncharged form and will remain behind in the sample well. Thus, no reducing agent migrates into the gel.

To maintain proteins in a reduced form during electrophoresis at neutral pH, it was found advantageous to use a reducing agent that would migrate into the gel at neutral pH. Sodium Bisulfite (2–10 mM) was found to maintain a reducing environment in the gel during electrophoresis. Fully reduced TGA (or similar negatively charged thiols) give similar results at comparable concentrations. However, partially oxidized TGA will promote partial oxidation of protein thiols. Because reduction (oxidation) of protein thiols will take place via disulfide interchange, the ratio of reduced to oxidized thiols in the protein will substantially reflect the ratio of reduced to oxidized thiols in the TGA. Conversely, sulfite oxidizes to sulfate, which does not participate in redox reactions under conditions found in the gel. Therefore, regardless of the sulfite/sulfate ratio in a partially oxidized preparation of sulfite, as long as sufficient sulfite remains, proteins will be protected against thiol oxidation.

It was also found that TRIS could be substituted for Bis-Tris in the running buffer with no visible effect on the separation quality. Bis-Tris may be preferred where the protein will be intentionally modified post-separation. Bis-Tris is a tertiary amine and will not interfere with the protein modifying agents which react through primary amines. TRIS, however is the preferred choice for routine use, because it is available at significantly lower cost than Bis-Tris.

While the invention has been explained in relation to its preferred embodiments, it is to be understood that various modifications thereof will become apparent to those skilled in the art. The foregoing disclosure is not intended or to be construed to limit the present invention, or to otherwise exclude any such other embodiments, adaptions, variations and equivalent arrangements, the present invention being limited only by the claims appended hereto and the equivalents thereof.

We claim:

1. An apparatus for gel electrophoresis comprising:

a precast polyacrylamide electrophoresis gel uniformly saturated prior to electrophoresis with a gel buffer solution comprising a monovalent organic amine or substituted amine with a pK near neutrality, titrated with HCl to a pH of between about pH 5.5 and about pH 7.5;

wherein said gel is adapted to be stored without degradation of said gel due to polyacrylamide hydrolysis;

and wherein said gel has two ends;

one end of the gel being in contact with an anode buffer solution;

the other end the gel being in contact with a cathode buffer solution;

said cathode buffer comprising a solution of a zwitterionic buffer selected from the group consisting of 3-[N-Morpholino]propanesulfonic acid, 2-(N-Morpholino)ethanesulfonic acid, [N-(2-Acetomido)]-2-aminoethanesulfonic acid, 2-[N-Morpholino]-2-hydroxypropanesulfonic acid, N-Tris-(hydroxymethyl)-2-ethanesulfonic acid, N-2-Hydroxyethyl-piperazine-n-2-ethanesulfonic acid and 3-(N-tris-(Hydroxymethyl)methylamino)-2-hydroxypropanesulfonic acid, titrated to between about pH 5.5 and about pH 5.5 with sodium hydroxide or an organic base; and said anode buffer comprising tris(hydroxy methyl)aminomethane.

2. The apparatus of claim 1 wherein said gel buffer comprises Bis-(2-hydroxyethyl)iminotris(hydroxymethyl)methane.

3. The apparatus of claim 2 wherein the cathode buffer solution comprises sulfite.

4. The apparatus of claim 2 wherein the cathode buffer solution comprises a reagent that is negatively charged at neutral pH and wherein the reagent comprises a thiol.

5. The apparatus of claim 2 wherein the cathode buffer solution comprises thioglycolic acid.

6. An apparatus for gel electrophoresis comprising:

a precast polyacrylamide electrophoresis gel uniformly saturated prior to electrophoresis with a gel buffer solution comprising Bis-(2-hydroxyethyl)iminotris(hydroxymethyl)methane titrated with HCl to a pH of between about pH 5.5 and about pH 7.5;

wherein said gel is adapted to be stored without degradation of said gel due to polyacrylamide hydrolysis;

said gel having two ends;

one end of the gel being in contact with an anode buffer solution;

the other end of the gel being in contact with a cathode buffer solution;

said cathode buffer comprising a solution of a zwitterionic buffer selected from the group consisting of 3-[N-Morpholino]propanesulfonic acid, 2-(N-Morpholino)ethanesulfonic acid, [N-(2-Acetomido)]-2-aminoethanesulfonic acid, 2-[N-Morpholino]-2-hydroxypropanesulfonic acid, N-Tris-(hydroxymethyl)-2-ethanesulfonic acid, N-2-Hydroxyethyl-piperazine-n-2-ethanesulfonic acid and 3-(N-tris-(Hydroxymethyl)methylamino)-2-hydroxypropanesulfonic acid, titrated to between about pH 5.5 and about pH 8.5 with sodium hydroxide or an organic base; and said anode buffer comprising tris(hydroxy methyl)aminomethane.

7. The apparatus of claim 6 wherein the cathode buffer comprises sulfite.

8. The apparatus of claim 6 wherein the cathode buffer comprises a reagent that is negatively charged at neutral pH and wherein the reagent comprises a thiol.

9. The apparatus of claim 6 wherein the cathode buffer comprises thioglycolic acid.

10. An apparatus for gel electrophoresis comprising:

a precast polyacrylamide electrophoresis gel uniformly saturated prior to electrophoresis with a gel buffer solution comprising a monovalent organic amine or substituted amine with a pK near neutrality, titrated with HCl to a pH between pH 5.5 and about pH 7.5;

wherein said gel is adapted to be stored without degradation of said gel due to polyacrylamide hydrolysis;

said gel having two ends;

one end of the gel being in contact with an anode buffer solution;

the other end of the gel being in contact with a cathode buffer solution;

said cathode buffer comprising a reducing agent that is negatively charged at neutral pH wherein said reducing agent migrates into the electrophoresis gel during electrophoresis and maintains a reducing environment in the electrophoresis gel to inhibit the formation of disulfide bonds in a migrating protein during electrophoresis.

11. The apparatus of claim 10 wherein said reducing agent of said cathode buffer comprises sulfite.

12. The apparatus of claim 10 wherein said reducing agent of said cathode buffer comprises thioglycolic acid.

13. The apparatus of claim 10 wherein said reducing agent of said cathode buffer comprises a thiol.

14. The apparatus of claim 10 wherein said gel buffer comprises Bis-(2-hydroxyethyl)iminotris(hydroxymethyl)methane.

15. The apparatus of claim 14 wherein said anode buffer comprises tris(hydroxy methyl)amino-methane.

16. The apparatus of claim 15 wherein said reducing agent of said cathode buffer comprises sulfite.

17. The apparatus of claim 15 wherein said reducing agent of said cathode buffer comprises thioglycolic acid.

* * * * *

UNITED STATES PATENT AND TRADEMARK OFFICE
CERTIFICATE OF CORRECTION

PATENT NO. : 5,578,180
DATED : November 26, 1996
INVENTOR(S) : Sheldon Engelhorn et al.

It is certified that error appears in the above-indentified patent and that said Letters Patent is hereby corrected as shown below:

Col. 7, line 6, change "pK" to -- $pK_a$ --.

Col. 7, line 7, change "about pH 5.5 and about" to -- pH 5.5 and --.

Col. 7, line 25, delete "between".

Col. 7, line 26, change "5.5" to -- 8.5 --.

Col. 7, lines 45 to 46, change "about pH 5.5 and about" to -- pH 5.5 and --.

Col. 8, line 24, delete "about".

Col. 8, line 23, change "pK" to -- $pK_a$ --.

Signed and Sealed this

Twenty-seventh Day of July, 1999

Attest:

Q. TODD DICKINSON

*Attesting Officer*     *Acting Commissioner of Patents and Trademarks*